US005520656A

United States Patent [19]

Byrd

[11] Patent Number: 5,520,656
[45] Date of Patent: May 28, 1996

[54] MEDICAL TUBE/WIRE HOLDING DEVICE AND ASSOCIATED TUBE/WIRE HOLDING METHOD

[76] Inventor: Timothy N. Byrd, 1267 Old Cades Cove Rd., Townsend, Tenn. 37882

[21] Appl. No.: 412,896

[22] Filed: Mar. 29, 1995

[51] Int. Cl.[6] ..................................................... A61M 5/32
[52] U.S. Cl. ........................................... 604/180; 604/174
[58] Field of Search ..................................... 604/180, 174, 604/93, 264, 177, 178, 179, 180; 128/DIG. 26

[56] References Cited

U.S. PATENT DOCUMENTS

| | | |
|---|---|---|
| D. 310,721 | 9/1990 | Beisang, III . |
| 3,046,989 | 7/1962 | Hill . |
| 3,430,300 | 3/1969 | Doan .................................. 604/180 |
| 3,826,254 | 7/1974 | Mellor . |
| 3,927,676 | 12/1975 | Schultz . |
| 3,977,407 | 8/1976 | Coleman et al. . |
| 4,088,136 | 5/1978 | Hasslinger et al. ............... 128/DIG. 26 |
| 4,120,304 | 10/1978 | Moor . |
| 4,142,527 | 3/1979 | Garcia . |
| 4,165,748 | 8/1979 | Johnson . |
| 4,249,529 | 2/1981 | Nestor et al. . |
| 4,333,468 | 6/1982 | Geist . |
| 4,351,331 | 9/1982 | Gereg . |
| 4,489,723 | 12/1984 | Simons et al. . |
| 4,548,200 | 10/1985 | Wapner . |
| 4,583,976 | 4/1986 | Ferguson . |
| 4,617,017 | 10/1986 | Hubbard et al. ................ 128/DIG. 26 |
| 4,690,675 | 9/1987 | Katz . |
| 4,744,358 | 5/1988 | McGinnis . |
| 4,774,944 | 10/1988 | Mischinski . |
| 4,823,789 | 4/1989 | Beisang, III . |
| 4,836,200 | 6/1989 | Clark . |
| 4,932,943 | 6/1990 | Nowak . |
| 5,009,227 | 4/1991 | Nieuwstad . |
| 5,037,397 | 8/1991 | Kalt et al. . |
| 5,147,322 | 9/1992 | Bowen et al. ................... 128/DIG. 26 |
| 5,215,532 | 6/1993 | Atkinson . |
| 5,300,037 | 4/1994 | Delk et al. ............................. 604/180 |
| 5,304,146 | 4/1994 | Johnson et al. . |

Primary Examiner—Corrine M. Maglione
Assistant Examiner—N. Kent Gring
Attorney, Agent, or Firm—Pitts & Brittian

[57] ABSTRACT

A medical tube/wire holding device and method. The holding device (10) includes a flexible body (14) defining first and second end portions (16, 18), and defining an opening (20) therethrough disposed between the first and second end portions such that the body defines first and second engaging straps (22, 24) disposed on opposite sides of the opening (20) for engaging at least one medical tube (12) or wire. The holding device (10) also includes a mechanism for releasably securing the first end portion of the body of the device to a patient, and a mechanism for securing the first and second engaging straps about at least one medical tube or wire. The holding method includes the steps of releasably securing the first end portion (16) of the body (14) to the patient at a desired location, and positioning at least one medical tube or wire such that it traverses the body (14). The second end portion (18) of the device is then moved around the tube or wire and inserted through the opening (20) in the body such that the first and second engaging straps (22, 24) of the holding device engage, and hold the position of, the tube or wire. The second end portion (18) of the body is then secured in place such that it is prohibited from moving back through the opening (20) in the body (14).

11 Claims, 5 Drawing Sheets

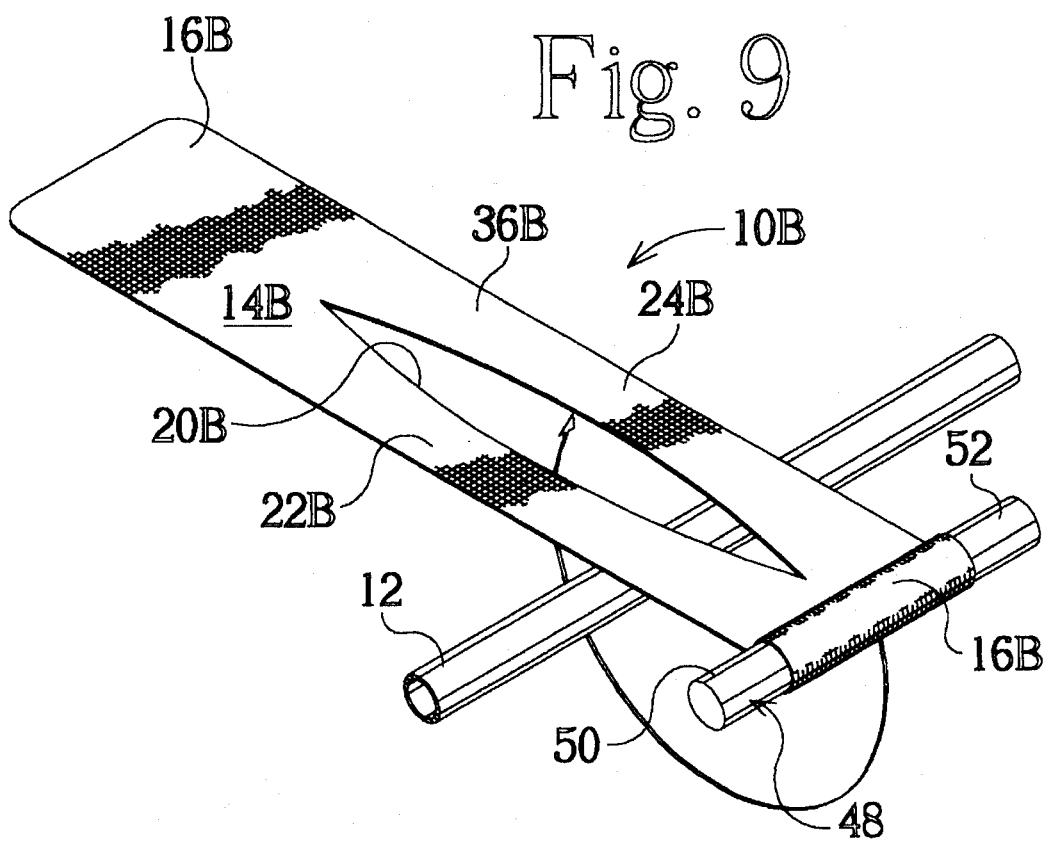
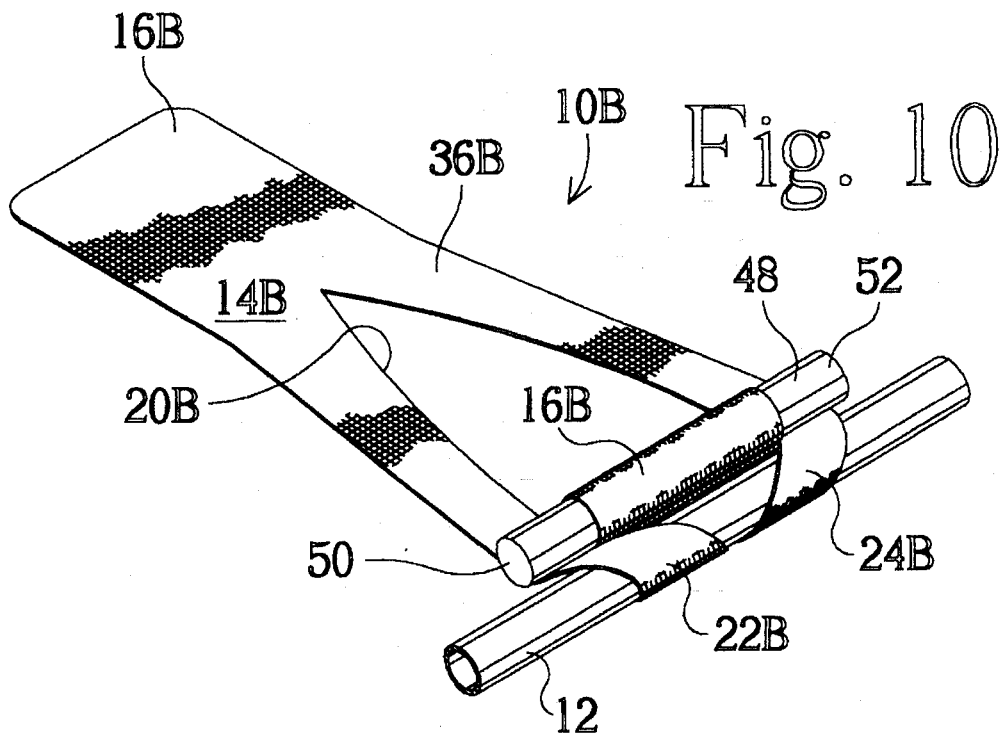

MEDICAL TUBE/WIRE HOLDING DEVICE AND ASSOCIATED TUBE/WIRE HOLDING METHOD

TECHNICAL FIELD

This invention relates to a medical tube/wire holding device which is releasably secured to the body of a patient, or the clothing of the patient, for securing the position of one or more tubes or wires used in a medical procedure, and relates to an associated tube/wire holding method. In this particular invention the tube holding device includes a flexible body having first and second opposite end portion and an opening therein bordered by a pair of engaging straps.

BACKGROUND ART

Numerous medical and surgical procedures require the use of tubes for carrying fluids between a patient and various medical devices. Indeed, it is not unusual for a plurality of such tubes to be used simultaneously on a single patient for intubation of the patient or other purposes. Further, wires often must be routed between a patient and various medical equipment. Accordingly, it is often desirable to releasably secure medical tubes and wires to the skin surface of the patient, or to the patient's clothing, in order to insure that the tubes are maintained in the desired position. This is particularly desirable when a tube is being use for intubation of the patient and inadvertent withdrawal or movement of the tube could jeopardize the health of the patient or cause the patient discomfort. Accordingly, various tube/wire holding devices have been designed for maintaining the position of medical tubes and wires. For example, M. C. Johnson Co., Inc., of Naples, Fla., manufactures tube holding devices under the trademark Cath-Secure® which feature a butterfly base configuration which secures to a patent with adhesive, and features a hook and loop fastener for engaging the tube(s). However, such fasteners can be difficult to use and expensive to manufacture. Moreover, the components of hook and loop fasteners can trap body fluids and other contaminants, making such holding devices undesirable for extended use. Other tube holding devices are disclosed in U.S. Pat. Nos. 5,215,532; 5,037,397; 4,932,943; 4,823,789; 4,583,976; 4,333,468; 4,142,527; 3,927,676; 3,826,254; and 3,046,989.

Therefore, it is an object of the present invention to provide a medical tube/wire holding device which is releasably secured to the body of a patient for securing the position of one or more tubes and/or wires used in medical procedures.

It is another object of the present invention to provide a method for maintaining the position of one or more medical tubes and/or wires relative to the body of a patient.

Yet another object of the present invention is to provide a tube/wire holding device which is easy to use and which can be repetitively used to releasably engage one or more medical tubes or wires.

Still another object of the present invention is to provide a medical tube/wire holding device which is easy to use and inexpensive to manufacture.

SUMMARY OF THE INVENTION

The present invention provides a medical tube/wire holding device for securing to a patient, or the clothing of a patient, and for engaging and maintaining the desired position of at least one medical tube and/or wire. The tube holding device includes a flexible body having a lower surface and defining first and second end portions. The body of the holding device is provided with an opening therethrough disposed between the first and second end portions such that the body defines first and second engaging straps disposed on opposite sides of the opening for engaging, and securing the position of, at least one medical tube or wire. A mechanism is provide for releasably securing the first end portion of the body of the holding device to the patient or the patient's clothing. In one embodiment this mechanism is an adhesive-covered surface portion provided on the lower surface of the body proximate the first end portion of the body.

In accordance with the method of the present invention the first end portion of the body of the holding device is releasably secured to the skin or clothing of the patient at a desired location. At least one medical tube or wire is then positioned such that the tube or wire traverses the body of the holding device, and the second end portion of the holding device is moved around the tube and inserted through the opening in the body such that the first and second engaging straps of the holding device engage, and maintain the position of, the medical tube or wire. The second end portion, having been received through the body of the device is then secured in position such that it is prohibited from moving back through the opening in the holding device and such that the medical tube or wire is maintained by the holding device.

In this regard, the holding device includes a mechanism for securing the first and second engaging straps about the medical tube or wire after the second end portion is received through the opening in the body. In one embodiment this mechanism includes a further adhesive-covered surface portion provided on the lower surface of the body proximate the second end portion for releasably bonding the second end portion to the patient, or the patient's clothing whereby the second end portion is releasably prohibited from moving through the opening in the body. In another embodiment, such mechanism includes a locking bar carried by the second end portion of the body. The locking bar defines first and second opposite end portions which extend beyond the body for releasably engaging the first and second engaging straps, respectively, such that the second end portion is releasably prohibited from moving through the opening in the body.

BRIEF DESCRIPTION OF THE DRAWINGS

The above mentioned features of the invention will be more clearly understood from the following detailed description of the invention read together with the drawings in which:

FIG. 9 illustrates a perspective view of the top of another alternate embodiment of the tube/wire holding device of the present invention.

FIG. 10 illustrates a perspective view of the top of another alternate embodiment of the tube/wire holding device of the present invention.

BEST MODE FOR CARRYING OUT THE INVENTION

Figure 1:
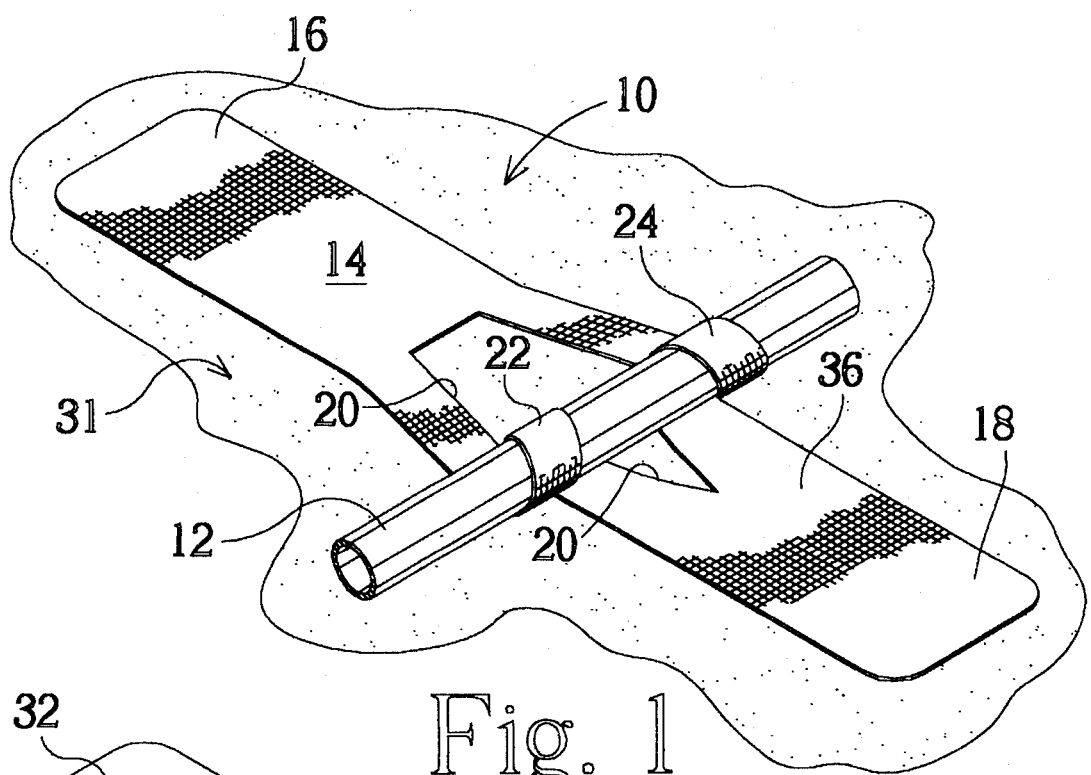
FIG. 1 illustrates a perspective view of the top of a tube/wire holding device of the present invention.

A tube/wire holding device incorporating various feature of the present invention is illustrated generally at 10 in FIGS. 1–4. The hold device 10 is designed to be releasably secured to a patient, or a patient's clothing and to releasably engage, and maintain the position of, medical tubes and/or wires, such as, for example, the illustrated tube 12. The holding device 10 includes a body 14 fabricated of a thin flexible material, such as, for example, a laminated spun bond polypropylene fabric.

The body 14 defines first and second opposite end portions 16 and 18, respectively, and is provided with an opening 20 therethrough which is disposed between the opposite end portions 16 and 18. As illustrated in FIGS. 1–4, in the preferred embodiment the opening 20 defines an elongated slot, substantially centrally disposed in the body 14, such that the body 14 includes a pair of engaging straps 22 and 24. However, it will be recognized from the discussion below that the opening 20 can define various geometric configurations, and the illustrated opening 20 is merely illustrative of one preferred embodiment. For example, the opening 20 could be simply a slit defined in the body 14.

Figure 2:
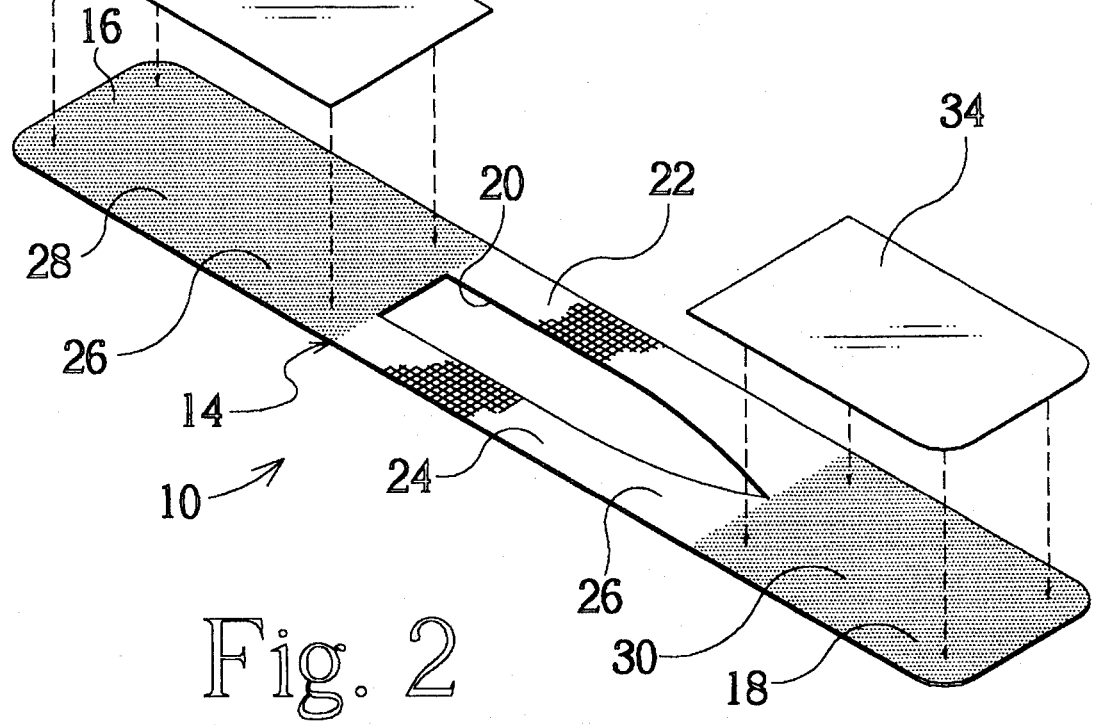
FIG. 2 illustrates a perspective view of the bottom of a tube/wire holding device of the present invention.

In the embodiment of the holding device 10 illustrated in FIGS. 1–4 both of the opposite end portions 16 and 18 are provided with mechanisms for releasably securing the end portions 16 and 18 to the body of a patient. In this regard, references herein to securing or bonding the device 10 to the patient are intended to include securing the device to the clothing of the patient. As illustrated in FIG. 2, in one preferred embodiment the body 14 of the device 10 defines a lower surface 26 having first and second adhesive-covered surface portions 28 and 30, respectively, with the adhesive covering at least substantial portions of the end portions 16 and 18, respectively. As is discussed further below, the adhesive-covered surface portions 28 and 30 serve to releasably secure the body 14 to the skin 31 or clothing of the patient. Further, protective panels 32 and 34 can be provided to cover the adhesive-covered surface portions 28 and 30 prior to use such that the bonding ability of the adhesive is not compromised.

Figure 3:
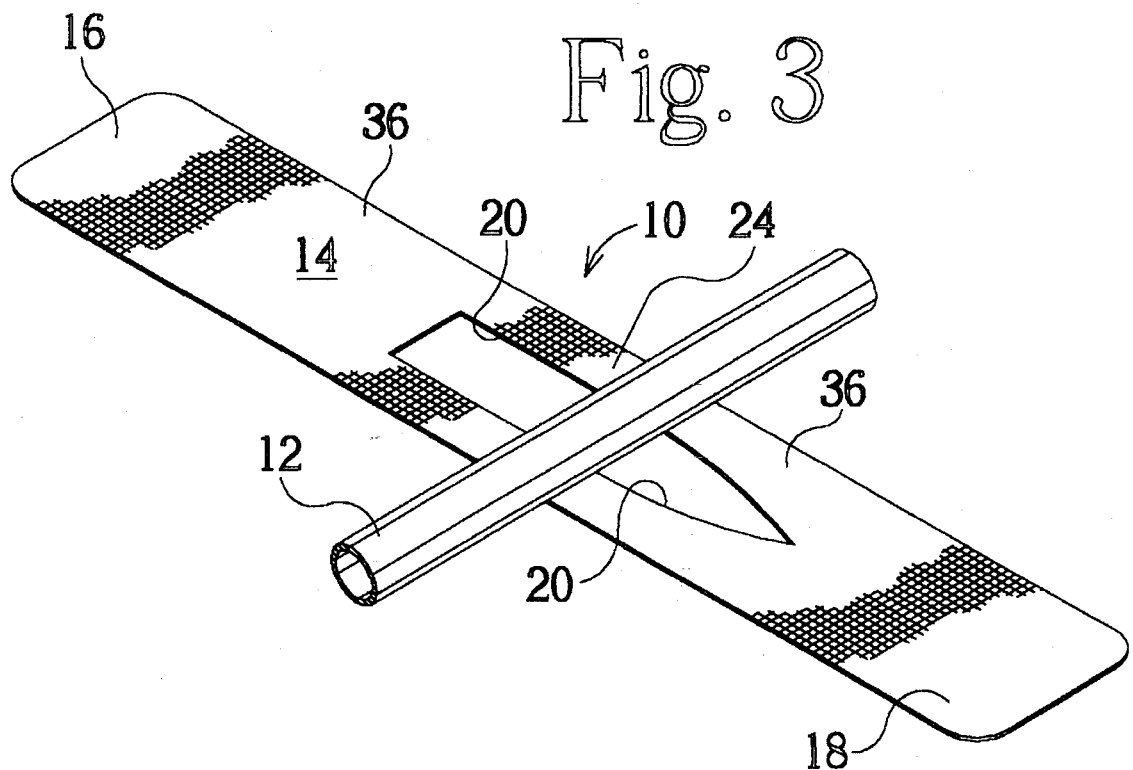
FIG. 3 illustrates a perspective view of the top of a tube/wire holding device of the present invention.
Figure 4:
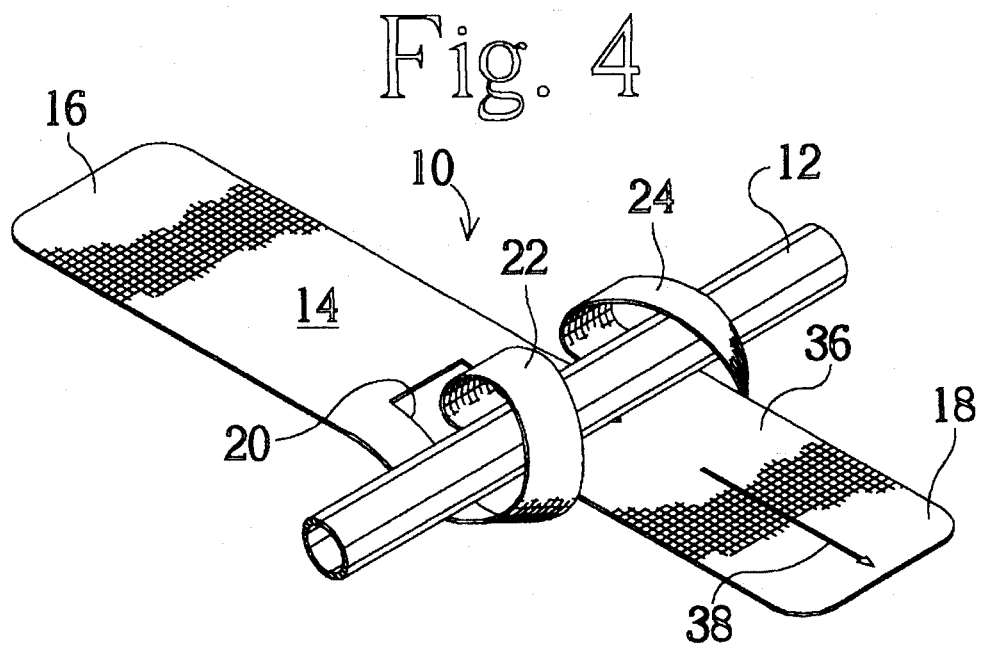
FIG. 4 illustrates a perspective view of the top of a tube/wire holding device of the present invention.

In accordance with the tube/wire holding method of the present invention a tube or wire is secured in the desired position on the patient by securing the first end portion 16 to the patient at the desired location using the adhesive-covered surface portion 28. The tube 12 or wire is then placed across the upper surface of the body 14 as illustrated in FIG. 3, and the second end portion 18 of the body 14 is moved around the tube 12 or wire and inserted through the opening 20 as illustrated in FIG. 4. Once received through the opening 20 the second end portion 18 of the body 14 is pulled in the direction of arrow 38 (see FIG. 4) in order to tighten the engaging straps 22 and 24 about the tube 12. The second end portion 18 of the body 14 is then secured to the patient using the adhesive-covered surface portion 30 such that the tube 12 or wire is secured in the straps 22 and 24, as illustrated in FIG. 1.

It will be recognized that the holding device 10 can be used to secure more than one tube 12, and/or wire, if desired. Further, releasing the tube 12, or wir(e) is simply a matter of removing the second end portion 18 from the patient's skin or clothing and passing the second end portion 18 back through the opening 20. If desired, the first end portion 16 can remain secured to the patient, such that the tube(s) 12 or wires can be subsequently repositioned in the holding device 10.

Figure 5:
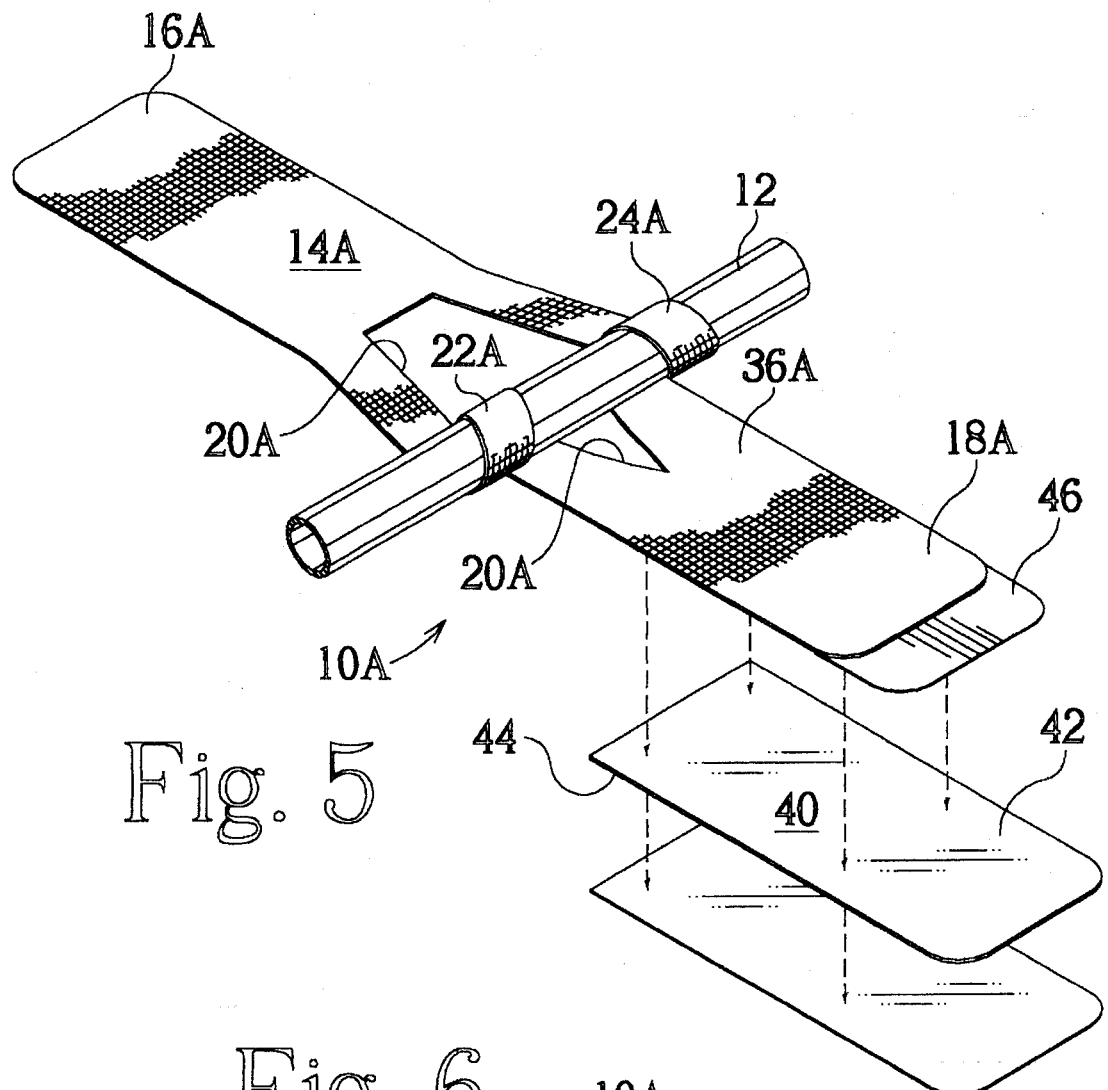
FIG. 5 illustrates a perspective view of the top of an alternate embodiment of the tube/wire holding device of the present invention.
Figure 6:
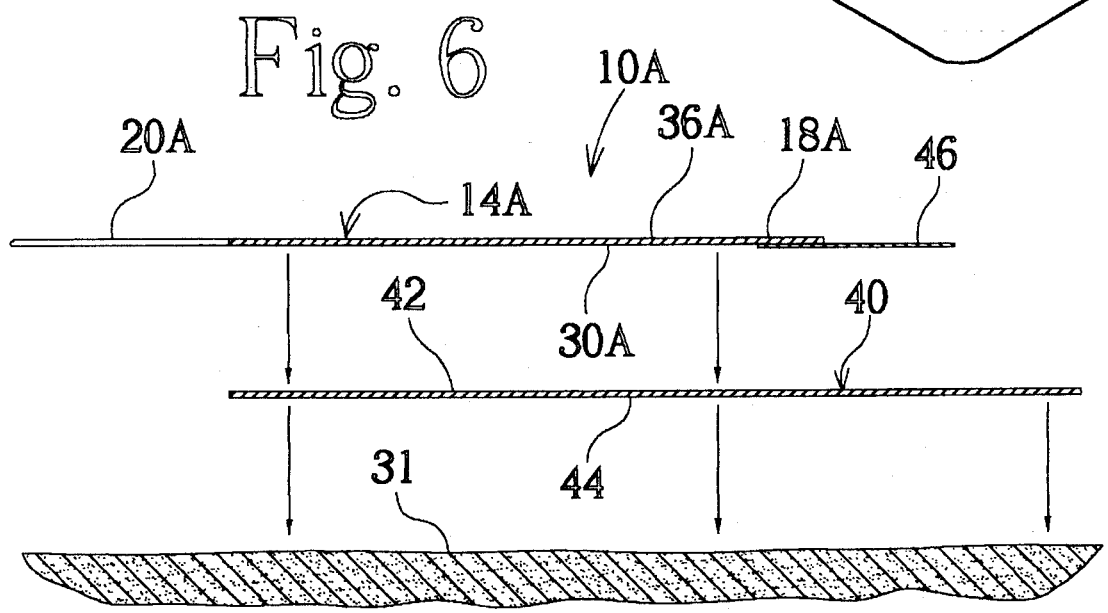
FIG. 6 illustrates a partial side elevation view, in section, of an alternate embodiment of the tube/wire holding device of the present invention.
Figure 7:
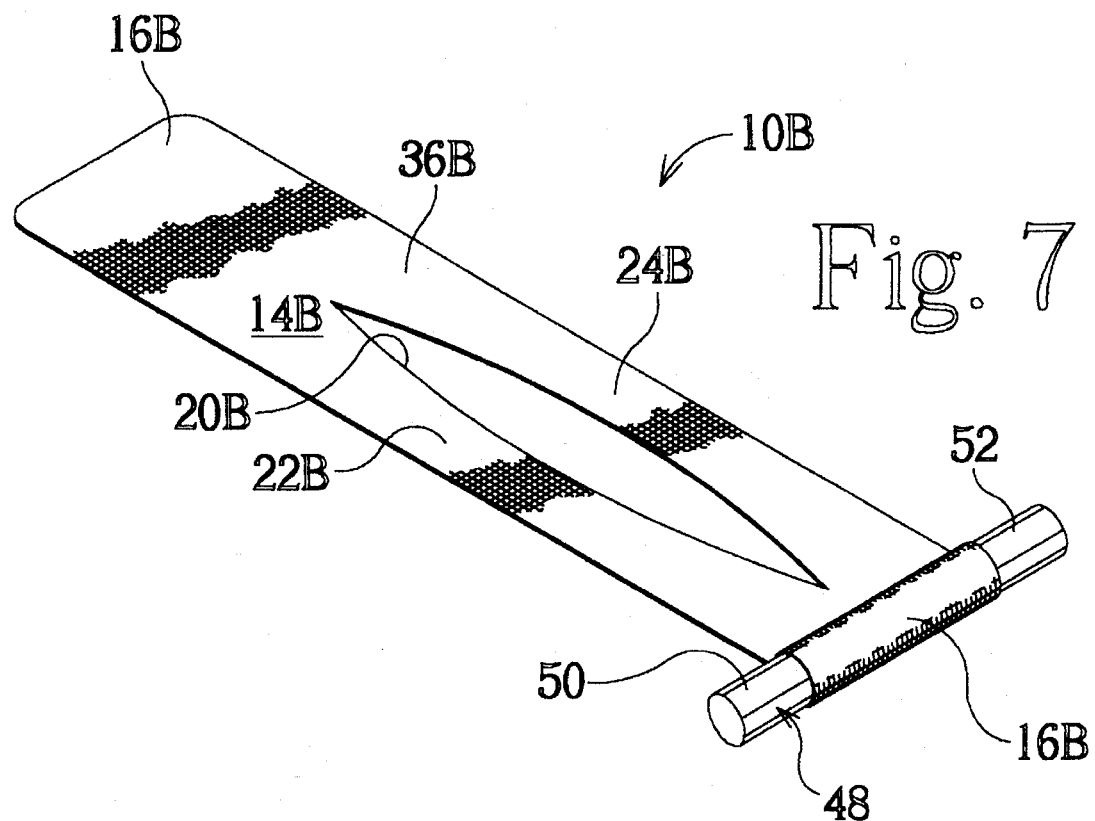
FIG. 7 illustrates a perspective view of the top of another alternate embodiment of the tube/wire holding device of the present invention.
Figure 8:
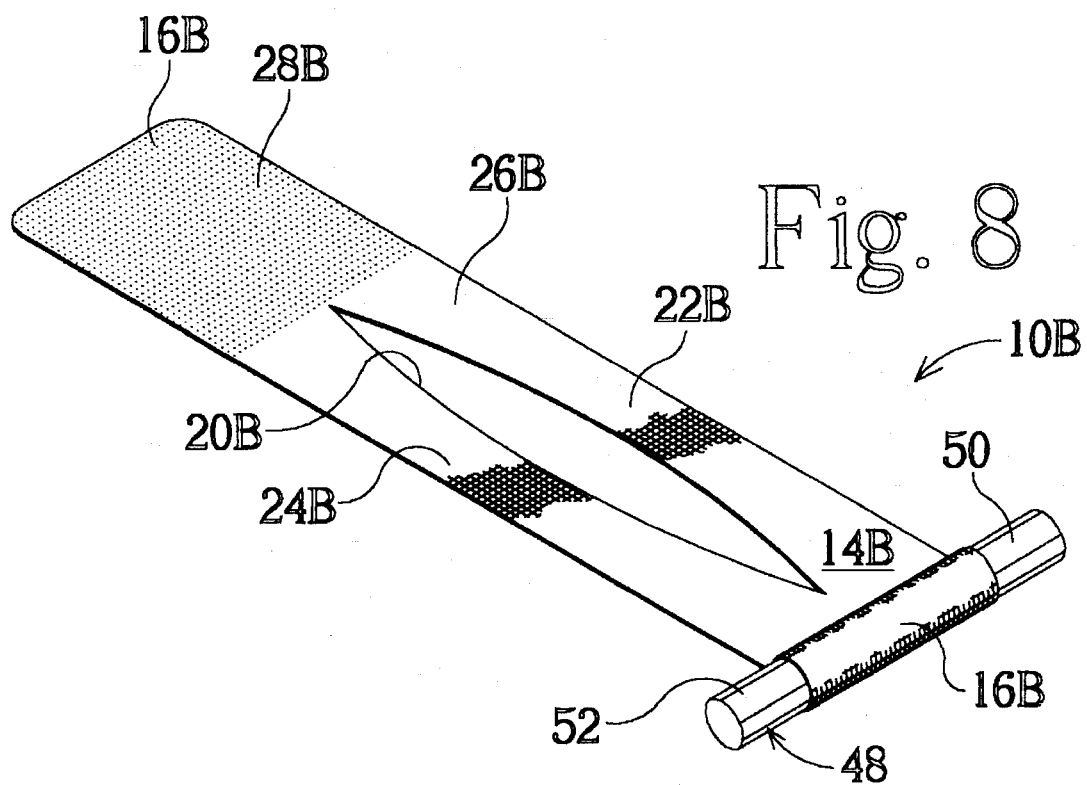
FIG. 8 illustrates a perspective view of the bottom of another alternate embodiment of the tube/wire holding device of the present invention.

In FIGS. 5–6 an alternate embodiment of the tube/wire holding device of the present invention is illustrated generally at 10A. For convenience, features and components of the holding device 10A which are common to the holding device 10 described above are references with common numerals followed by the alphabetic character "A". As illustrated, the second end portion 18A of the holding device 10A is provided with a bonding panel 40 which defines an upper bonding surface 42 to which the second adhesive-covered surface portion 30A is releasably secured. In the preferred embodiment the bonding surface 42 is a smooth, substantially non-porous surface which allows repetitive engagement with the adhesive-covered surface portion 30A without significant degradation of the bonding strength of the adhesive. The lower surface 44 of the bonding panel 40 is coated, at least in substantial part, with an adhesive for releasably securing the panel 40 to the patient.

The holding device 10A is utilized in substantially the same fashion as described above with respect to the holding device 10. However, rather than the second end portion 18A being secured directly to the patient, the lower surface 44 of the bonding panel 40 is secured to the patient. Accordingly, when release of the tube 12 or wire is desired the second end portion 18A can be readily release by pulling it from the bonding surface 42 of the bonding panel 40, while the bonding panel 40 remains in place. When the tube 12 or wire must be replaced in the tube holder 10A, the bonding panel is already in place to again releasably receive the second end portion 18A of the holding device 10A. Thus, it will be recognized that the tube(s) 12 and or wire(s) can be repetitively secured in, and released from, the holding device 10A without unduly degrading the bonding strength of the adhesive of the second adhesive-covered bonding surface 30A.

It will be noted that in order to facilitate the release of the second end portion 18A from the bonding panel 40 the second end portion 18A can be provided with an adhesive-free tab 46 for the grasping of the second end portion 18A. It will also be noted that the bonding panel 40 can be provided with a protective panel 34A to protect the adhesive of the lower surface 44 of the panel 40 prior to use. Further, although not shown in the Figures, it is contemplated that a bonding panel such as the panel 40 can be provided for the first end portion 16A.

In FIGS. 7–10 another alternate embodiment of the tube/wire holding device of the present invention is illustrated generally at 10B. For convenience, features and components of the holding device 10B which are common to the holding device 10 described above are references with common numerals followed by the alphabetic character "B". As illustrated, the tube holding device 10B utilizes an alternate mechanism for securing the 12 or wire in the engaging straps 22B and 24B. In this regard, the second end portion 18B carries a locking bar 48 defining opposite end portions 50 and 52 which extend beyond the edge of the body 14B.

In accordance with the method associated with the holding device 10B, the first end portion 16B is secured to the patient at the desired location through the use of the adhesive covered surface portion 28B. In order to secure the tube 12 or wire in the holding device 10B, the second end portion 18B of the body 14B is directed around the tube 12 or wire as illustrated in FIG. 9, and the locking bar 48 is inserted through the opening 20B in the body 14B. As illustrated in FIG. 10, the locking bar 48 is then positioned such that the end portion 50 of the bar 48 engages the engaging strap 22B and the end portion 52 engages the engaging strap 24B, thereby prohibiting the bar 48 from moving back through the opening 20B. As a result, the straps 22B and 24B are releasably secured about the tube 12 or wire, and serve to hold the tube 12 or wire, in place.

In order to release the tube 12 or wire from the holder 10B, the locking bar 48 is repositioned such that one of the end portions 50 or 52 can be directed through the opening 20B, and the bar 48 is moved through the opening 20B such that the straps 22B and 24B no longer serve to secure the tube 12 or wire. Of course, when utilizing the device 10B the tube 12 and or wires can be secured and release whenever desired while the holding device 10B remains secured to the patient. Further, it will be understood that the holding device 10B can engage and secure a plurality of tubes 12 if desired.

In light of the above it will be recognized that the present invention provides a medical tube/wire holding device having great advantages over the prior art. The tube/wires holding device can be releasably secured at various locations on the body of the patient, and can releasably engage one or more medical tubes and/or wires. Moreover, the holding device and associated method are easy to use, and allow medical tubes and wires to be quickly secured and released. However, while a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A medical tube/wire holding device for securing to a patient and for engaging and maintaining the desired position of at least one medical tube/wire, said holding device comprising:

a flexible body having a lower surface and defining first and second end portions, said body further defining an opening therethrough disposed between said first and second end portions such that said body defines first and second engaging straps disposed on opposite sides of said opening for engaging, and securing the position of, at least one medical tube/wire as said second end portion of said body is directed around at least one medical tube/wire and received through said opening;

a mechanism for releasably securing said first end portion of said body to the patient; and a mechanism for securing said first and second tube engaging straps about at least one medical tube/wire after said second end portion of said body is received through said opening in said body, said mechanism for securing said first and second engaging straps about at least one medical tube/wire including a locking bar carried by said second end portion of said body, said locking bar defining first and second opposite end portions extending beyond said body for releasably engaging said first and second engaging straps, respectively, whereby said second end portion is releasably prohibited from moving through said opening in said body.

2. A medical tube/wire holding method for releasably securing at least one medical tube/wire to a patient so as to maintain the desired position of the medical tube/wire, said method utilizing a holding device having a body defining first and second opposite end portions and an opening therethrough disposed between the first and second opposite end portions such that the body defines first and second engaging straps disposed on opposite sides of the opening, said method comprising the steps of:

releasably securing a lower surface of the first end portion of the body of the holding device to the patient at a desired location;

positioning at least one medical tube/wire such that said medical tube/wire traverses an upper surface of the body of the holding device;

moving the second end portion of the holding device about the medical tube/wire and inserting the second end portion of the holding device through the opening such that the upper surfaces of the first and second engaging straps of the holding device engage, and hold the position of, the medical tube/wire; and releasably securing a lower surface of the second end portion of the body of the holding device to the patient at a selected location such that the second end portion is prohibited from moving back through the opening in the holding device such at the medical tube/wire is maintained by the holding device.

3. The medical tube/wire holding method of claim 2 wherein said step of securing a lower surface of the first end portion of the body of the holding device to the patient includes releasably bonding the first end portion of the body to the patient with an adhesive-covered surface portion provided on the lower surface of the first end portion of the body of the holding device.

4. The medical tube/wire holding method of claim 3 wherein said step of releasably securing a lower surface of the second end portion of the body of the holding device includes releasably securing the second end portion of the body to the patient with an adhesive-covered surface portion provided on the lower surface of the second end portion of the body of the holding device.

5. The medical tube/wire holding method of claim 2 wherein said step of releasably securing a lower surface of the second end portion of the body of the holding device includes releasably securing the second end portion of the body to the patient with an adhesive-covered surface portion provided on the lower surface of the second end portion of the body of the holding device.

6. A medical tube/wire holding device for securing to a patient and for engaging and maintaining the desired position of at least one medical tube/wire, said holding device comprising:

a flexible body having a lower surface and defining first and second end portions, said body further defining an opening therethrough disposed between said first and second end portions such that said body defines first and second engaging straps disposed on opposite sides of said opening for engaging, and securing the position of, at least one medical tube/wire as said second end portion of said body is directed around at least one medical tube/wire and received through said opening;

a mechanism for releasably securing said first end portion of said body to the patient including an adhesive-covered surface portion provided on said lower surface of said body proximate said first end portion of said body for releasably bonding said first end portion to the patient; and a mechanism for securing said first and second tube engaging straps about at least one medical tube/wire after said second end portion of said body is received through said opening in said body including a locking bar carried by said second end portion of said body, said locking bar defining first and second opposite end portions extending beyond said body for releasably engaging said first and second engaging straps, respectively, whereby said second end portion is releasably prohibited from moving through said opening in said body.

7. A medical tube/wire holding method for releasably securing at least one medical tube/wire to a patient so as to maintain the desired position of the medical tube/wire, said method utilizing a holding device having a body defining first and second opposite end portions and an opening therethrough disposed between the first and second opposite end portions such that the body defines first and second engaging straps disposed on opposite sides of the opening, said method comprising the steps of:

releasably securing the first end portion of the body of the holding device to the patient at a desired location;

positioning at least one medical tube/wire such that said medical tube/wire traverses the body of the holding device;

moving the second end portion of the holding device about the medical tube/wire and inserting the second end portion of the holding device through the opening such that the first and second engaging straps of the holding device engage, and hold the position of, the medical tube/wire; and releasably securing the position of the second end portion of the holding device such that the second end portion is prohibited from moving back through the opening in the body of the holding device such that the medical tube/wire is maintained by the holding device, said step including placing the first and second end portions of a locking bar carried by the second end portion of the body in contact with the first and second engaging straps, respectively, whereby the second end portion is releasably prohibited from moving through the opening in the body of the holding device such that the medical tube/wire is maintained in position by the holding device.

8. A medical tube/wire holding device for securing to a patient and for engaging and maintaining the desired position of at least one medical tube/wire, said holding device comprising:

a flexible body having a lower surface for being secured to the patient and an upper surface for engaging at least one medical tube/wire, said body defining first and second end portions, said body further defining an opening therethrough disposed between said first and second end portions such that said body defines first and second engaging straps disposed on opposite sides of said opening for engaging, and securing the position of, at least one medical tube/wire subsequent to said second end portion of said body being directed around said at least one medical tube/wire and received through said opening;

a mechanism for releasably securing said lower surface of said body proximate said first end portion of said body to the patient; and a mechanism for releasably securing said lower surface of said body proximate said second end portion of said body to the patient after said second end portion of said body has been received through said opening in said body and about said at least one medical tube/wire, whereby said upper surface of said body at said first and second tube engaging straps engages and secures the position of said at least one medical tube/wire, and whereby said lower surface of said body proximate said second end portion is releasably secured to said patient, thereby prohibiting said second end portion from moving back through said opening in said body and facilitating the securing of the position of said at least one medical tube/wire.

9. The medical tube/wire holding device of claim 8 wherein said mechanism for releasably securing said lower surface of said body proximate said first end portion of said body to the patient includes an adhesive-covered surface portion provided on said lower surface of said body proximate said first end portion of said body for releasably bonding said first end portion to said patient.

10. The medical tube/wire holding device of claim 8 wherein said mechanism for releasably securing said lower surface of said body proximate said second end portion of said body to the patient includes an adhesive-covered surface portion provided on said lower surface of said body proximate said second end portion of said body for releasably bonding said second end portion to said patient.

11. The medical tube/wire holding device of claim 8 wherein said mechanism for releasably securing said lower surface of said body proximate said first end portion of said body to the patient includes an adhesive-covered surface portion provided on said lower surface of said body proximate said first end portion of said body for releasably bonding said first end portion to said patient, and wherein said mechanism for releasably securing said lower surface of said body proximate said second end portion of said body to the patient includes an adhesive-covered surface portion provided on said lower surface of said body proximate said second end portion of said body for releasably bonding said second end portion to said patient.

* * * * *